(12) United States Patent
Jundt et al.

(10) Patent No.: US 8,381,731 B2
(45) Date of Patent: Feb. 26, 2013

(54) MEDICAL TUBING STABILIZATION DEVICE

(76) Inventors: Jonathon Sedrick Jundt, Houston, TX (US); Cheryl Lewis Jundt, Houston, TX (US)

(*) Notice: Subject to any disclaimer, the term of this patent is extended or adjusted under 35 U.S.C. 154(b) by 351 days.

(21) Appl. No.: 12/762,201

(22) Filed: Apr. 16, 2010

(65) Prior Publication Data

US 2011/0253146 A1    Oct. 20, 2011

(51) Int. Cl.
*A61M 16/00* (2006.01)
*A61M 15/08* (2006.01)
*A62B 9/06* (2006.01)
*A62B 7/00* (2006.01)

(52) U.S. Cl. ......... 128/207.17; 128/207.18; 128/207.14; 128/200.26; 128/200.24; 604/174

(58) Field of Classification Search ............. 128/200.24, 128/202.18, 207.17; 604/174, 180
See application file for complete search history.

(56) References Cited

U.S. PATENT DOCUMENTS

| | | | |
|---|---|---|---|
| 3,324,853 A * | 6/1967 | Czorny et al. ................. 604/162 |
| 3,630,195 A * | 12/1971 | Santomieri ................... 604/180 |
| 3,696,920 A * | 10/1972 | Lahay ............................ 206/370 |
| 3,826,254 A * | 7/1974 | Mellor ........................... 604/180 |
| 3,834,380 A * | 9/1974 | Boyd .............................. 604/180 |
| 4,018,221 A * | 4/1977 | Rennie ....................... 128/207.18 |
| 4,122,857 A * | 10/1978 | Haerr ............................. 604/180 |
| 4,333,468 A * | 6/1982 | Geist .............................. 604/180 |
| 4,370,978 A * | 2/1983 | Palumbo ........................ 602/26 |
| 4,569,348 A * | 2/1986 | Hasslinger .................... 604/179 |
| 4,583,976 A * | 4/1986 | Ferguson ...................... 604/174 |
| 4,665,566 A * | 5/1987 | Garrow ............................ 2/171 |
| 4,738,662 A * | 4/1988 | Kalt et al. ..................... 604/180 |
| 4,821,736 A * | 4/1989 | Watson ......................... 600/532 |
| 4,838,878 A * | 6/1989 | Kalt et al. ..................... 604/180 |
| 5,037,397 A * | 8/1991 | Kalt et al. ..................... 604/174 |
| 5,163,914 A * | 11/1992 | Abel .............................. 604/180 |
| 5,397,639 A * | 3/1995 | Tollini ........................... 428/343 |
| 5,480,719 A * | 1/1996 | Tollini ........................... 428/343 |
| 2006/0289011 A1* | 12/2006 | Helsel ....................... 128/207.17 |
| 2007/0289597 A1* | 12/2007 | Masella et al. ........... 128/207.18 |
| 2010/0298778 A1* | 11/2010 | Bracken et al. ............... 604/180 |
| 2010/0300434 A1* | 12/2010 | Hajarian et al. ......... 128/200.24 |

* cited by examiner

*Primary Examiner* — Annette Dixon
(74) *Attorney, Agent, or Firm* — Matthew J. Esserman

(57) ABSTRACT

A medical stabilization device that directs medical tubing onto a compressible foam block where it is attached and stabilized to the patient's body allowing it to be secured against excessive movement, tube dislodgement and positioned in a time efficient manner to prevent obstruction of patient treatment.

22 Claims, 4 Drawing Sheets

MEDICAL TUBING STABILIZATION DEVICE

BACKGROUND OF THE INVENTION

During surgery of the head and neck existing methods of securing nasotracheal tubing can be a hindrance to the surgeon, either obstructing access to or blocking a clear view of the surgical area. One of the methods used to direct the nasotracheal tubing away from the surgical area is to secure the tubing to the patient's head using operating room tape. This method results in a number of problems. It is difficult to readjust placement of the tape, difficult to remove the tape, and the patient's hair is pulled out when the tape is removed.

Another method is to place a towel between the nasotracheal tubing and the forehead. This method does not provide adequate support to stabilize the tubing if it is inadvertently contacted during surgery, and may result in an accidental extubation.

Another method involves custom cutting a piece of foam, however this is time consuming and non-standardized. The performance of this method is variable depending on the nature of the foam and on how well the foam is fashioned into a cushion for the tubing in each instance. The raw edges created by the cuts also impose a hazard of microscopic flecks of foam being dispersed and potentially contaminating the surgical area.

Accordingly, prior to the development of the present invention, positioning the nasotracheal tubing securely away from the surgical area has been laborious and lacking in predictable stability. Most importantly, other methods do not adequately prevent accidental extubation. The present invention solves the problems of the current methods in practice by implementing a substantially U-shaped foam block which provides a conduit onto which a nasotracheal tubing can be attached to keep the tubing stabilized and the surgical area of the face, neck, jaws, or oral area unobstructed. The foam block, or medical tubing stabilization device, may be retained to a flexible band that wraps around the head.

DETAILED DESCRIPTION

Figure 1:
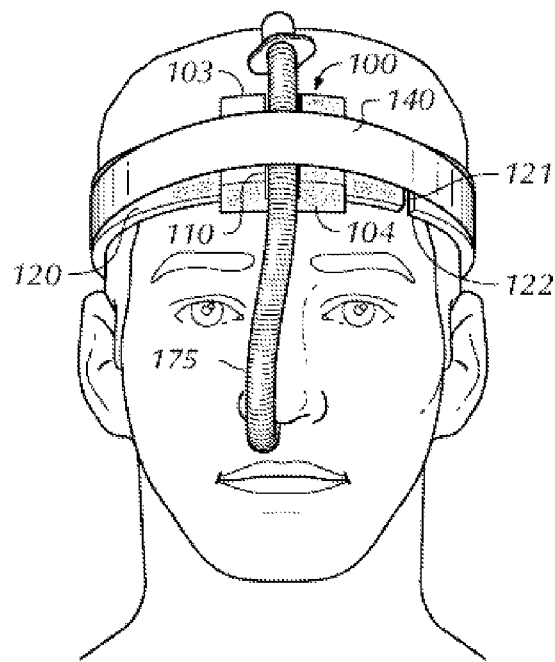
FIG. 1 is a superior view of a nasotracheal stabilization device mounted on a human head in accordance with an exemplary embodiment of the invention.

In accordance with the invention the foregoing advantages have been achieved through the present nasotracheal tubing stabilizing device. The present invention includes a substantially U-shaped compressible foam block. The block being comprised of opposing, substantially parallel superior and inferior surfaces and opposing substantially parallel anterior and posterior sides substantially perpendicular to the superior and inferior surfaces. The block further being comprised of opposing left and right sides and having a superior central depression, or channel, along its superior surface extending from the anterior to posterior surfaces, said channel having a depth of less than half of the length of the sides of the block. The length being determined as the distance from the anterior to the posterior surfaces.

Standard nasotracheal tube diameters vary from 4.5 mm to 8.5 mm depending on the size of the patient. In the preferred embodiment, the superior central depression would have a depth of half to twice the diameter of the tubing to be supported. A piece of operating room tape extending from the headband across the tubing resting in the foam block and attaching to the headband again on the other side provides maximum compression of the foam block resulting in a secure attachment. In another embodiment the tape may be substituted by a VELCRO®-type (hook and loop fastener-type) connecting surface. In another embodiment the tape may have an elastic property to securely position the tube in the channel. In another embodiment a friction fit may be used to position the tubing securely in the channel.

The substantially U-shaped foam block lies with the inferior surface toward the forehead of the patient, and the posterior side oriented toward the nose of the patient. The superior central depression is aligned with the nose in a vertical fashion across the plane of the face. The foam block can be attached to a flexible band with operating room tape or a VELCRO®-type, hook and loop fastener. The foam block is comprised of compressible foam that can deform to allow the block to envelop a nasotracheal tubing when the tubing is directed through the superior central depression and affixed to the foam block with standard operating room tape. Due to the compressible nature of the foam, the tubing is redirected from the surgical area with great stability, thus not impeding the progress of surgery to readjust the nasotracheal tubing. The band can also be fashioned of foam, soft cotton, flannel, or any other or similar material that would not induce pressure on tissues.

In another embodiment, the band and foam block may be used to position tubing and leads on other parts of a patient's body where there is a need to secure the devices to the surface of the patient's body without the extensive discomfort often caused by tape. The band, block, and channel of the device could be varied in size to secure medical devices to a patient's body to accommodate any needs for patient care such as intravenous lines, catheters, drain lines, electrocardiogram leads, etc.

In another embodiment, the block may be fashioned from a different material and covered on a plurality of surfaces with foam or cotton or other such materials to reduce pressure at the points of contact.

In another alternate embodiment, the block's left and right sides would angle out from the inferior surface of the block thus forming a trapezoidal prism shape. This would make the block wider on the inferior surface, where it contacts the patient's body, and narrower on the superior surface, where it secures the tubing. This shape would increase stability of the block on the curved surface of the patient's body, and still allow sufficient compressibility around the tubing to ensure its stable "grip" or positioning of the tubing.

In another alternate embodiment of the invention, the block could have a curved inferior surface to more closely adapt to the contour of the patient surface to be contacted, therefore providing more security from inadvertent displacement.

In another alternate embodiment of the invention, the block and band could be permanently attached as a single piece. In another embodiment the block and band could be molded as a single form. In this embodiment the band would extend substantially from one side of the block to be curved around the patient's extremity and joined to the other side of the block by surgical tape, VELCRO®-like (hook and loop fastener-like) closure, or some other suitable repositionable fastener.

In another alternate embodiment of the invention, reliefs could be cut out of the band to prevent compression of tissue such as ears when used as a headband. Such reliefs could also be used to avoid covering other areas of tenderness or injury on the patient.

In another alternate embodiment of the invention, hook and loop tape could be affixed to the surfaces of the foam block, and on both ends of the band, thus eliminating the need for operating room tape.

The present invention enables the surgeon to be unencumbered with nasotracheal tubing whilst performing surgery on the head, neck, and oral cavity. Further, the tubing is able to be repositioned or removed.

Figure 2:
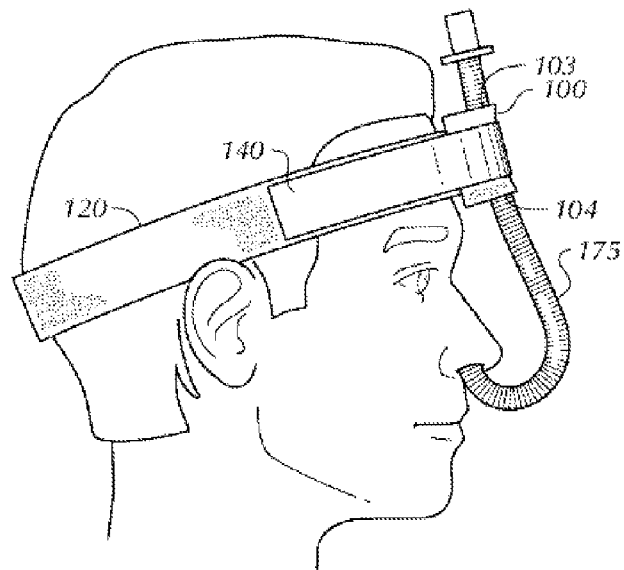
FIG. 2 is a side view of a human head with the nasotracheal stabilization device mounted thereon in accordance with an exemplary embodiment of the invention.

In FIG. 1 and FIG. 2 the medical tubing stabilization device is illustrated as worn on the head of the patient to stabilize nasotracheal tubing. A foam band 120 extends across the forehead, above the area of the ears, and around the back of the patient's head. The free end portions 121 and 122 of the band are shown above the left eye of the patient, but can be drawn together at another location along the anterior or side of the head. In the figure the ends are fastened together with standard operating room tape 140; but, one skilled in the art would appreciate other methods by which a repositionable connection can be accomplished. The U-shaped foam block 100 is connected to the band 120 at the location of the patient's forehead with the superior central channel 110 aligned with the nose in a vertical fashion across the frontal view of the face. The nasotracheal tubing 175 extends up from the nose and into the superior central depression 110 of the foam block 100. In the embodiment shown, the foam block 100 is positioned over the band 120 and a single piece of operating room tape 140 is used to secure the ends of the band 121 and 122 as well as securing the tubing 175 in the superior central depression 110. The compressible nature of the foam block 100 allows the tubing 175 to be securely enveloped and stabilized.

Figure 3:
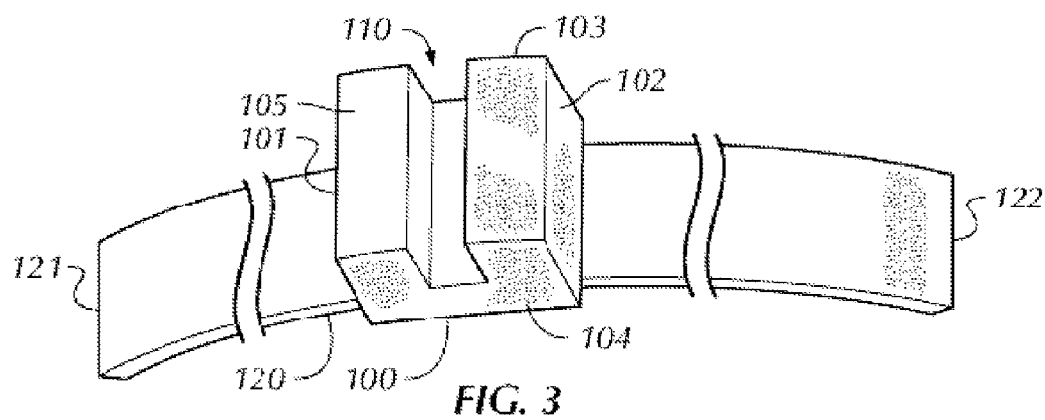
FIG. 3 is a perspective view of a medical tubing stabilization device in accordance with an exemplary embodiment of the invention.

FIG. 3 illustrates a foam block 100 having anterior 103 and posterior 104 sides that are perpendicular to the superior surface 105 into which a superior central depression or channel 110 is formed. The foam block 100 is situated atop the band 120 having ends 121 and 122. The left and right sides 101 and 102 of the foam block 100 can be formed at right angles to the superior and inferior sides 103 and 104.

Figure 4:
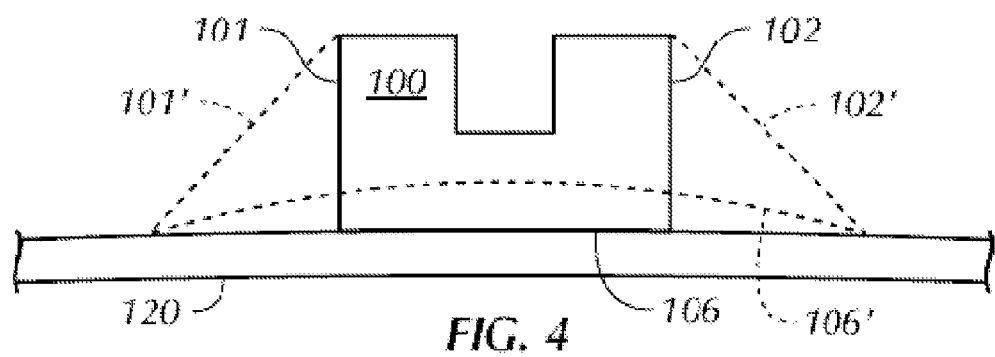
FIG. 4 is a posterior view of a medical tubing stabilization device in accordance with an exemplary embodiment of the invention.

FIG. 4 illustrates an alternative embodiment of the foam block 100 having sloping right and left sides 101' and 102', and inferior surface 106. In FIG. 4, the inferior surface 106' of the foam block is concaved. These features can increase stability and fit while decreasing pressure points.

FIG. 5 illustrates FIGS. 5A-5D illustrate several embodiments having alternative methods of securing the band, tubing, and block to the patient.

Figure 5A:
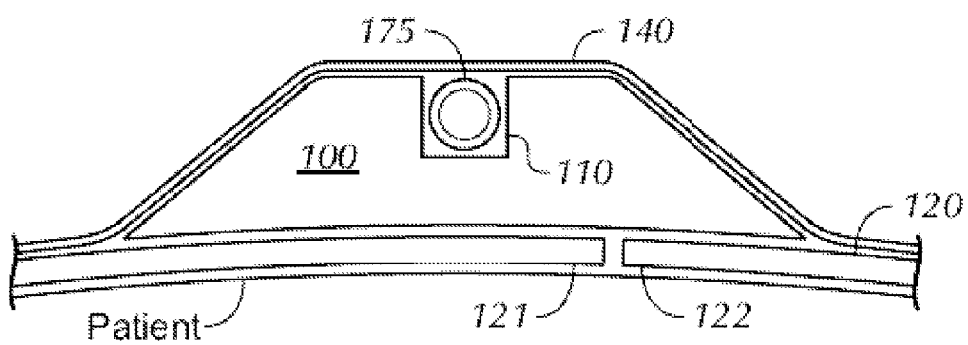
FIG. 5A through 5D are posterior views of a medical tubing stabilization device illustrating various configurations in accordance with exemplary embodiments of the invention.

FIG. 5A shows the band 120 positioned under the block 100. The ends of the band 121 and 122 are secured by tape 140 running over the block 100, over the tubing 175, which is in the channel 110, and to the band 120. In this configuration, the tape 140 secures the tubing to the block 100 preventing any slippage.

Figure 5B:
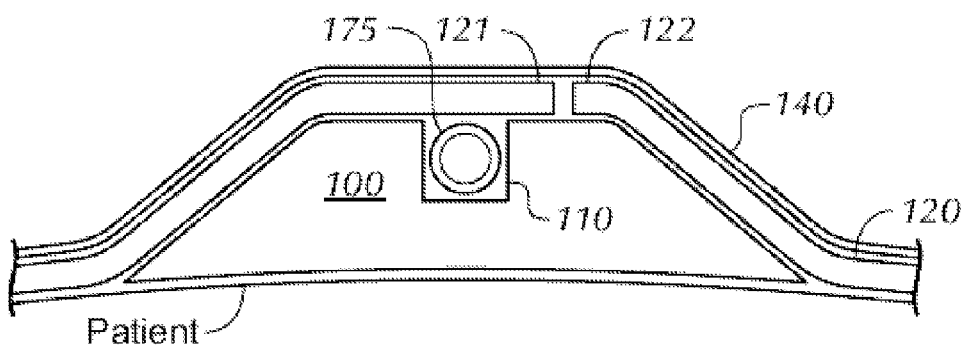

FIG. 5B shows the band 120 positioned over the block 100 and secured with tape 140. In this configuration, the tubing 175 is held to the block 100 through friction between the sides and bottom of the channel 110 and the band 120. In an alternative embodiment, an additional piece of tape 140 could be used to further secure the tubing 175 to the block 100.

Figure 5C:
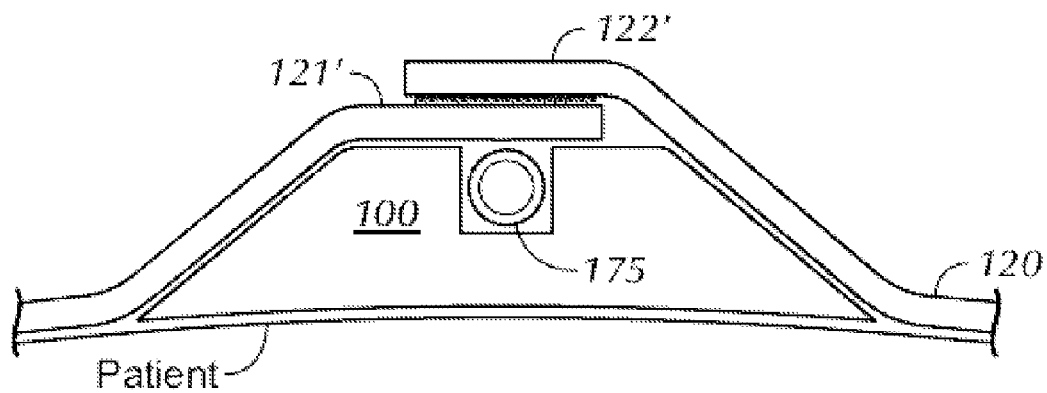

FIG. 5C shows the band 120 positioned over the block 100 and positioned by the use of a VELCRO®-type (hook and loop fastener-type) closure on the ends 121' and 122' of the band 120. As in FIG. 5B, the tubing 175 is secured either through friction or tape 140.

Figure 5D:
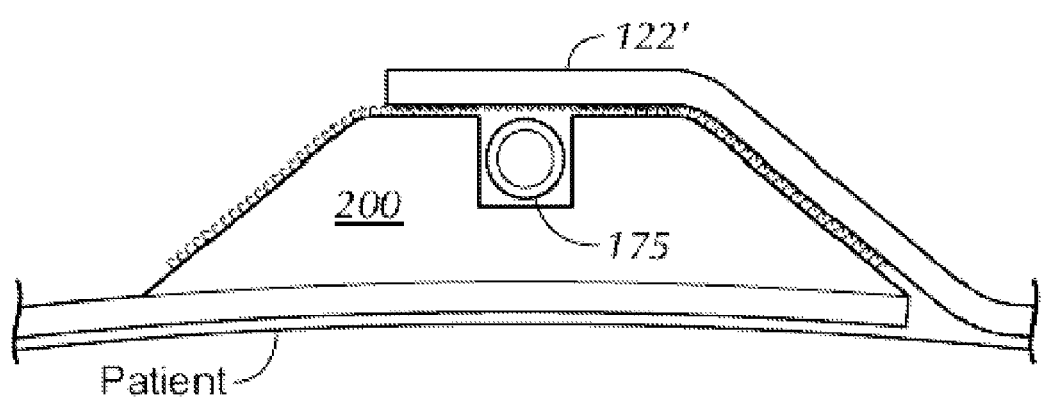

FIG. 5D shows the band and block as a single piece 200. In this embodiment, the block forms one end of the band. The superior surface of the block is coated in one half of a VELCRO®-type (hook and loop fastener-type) closure and the end of the band 122' is covered in the other half of a VELCRO®-type (hook and loop fastener-type) closure. In another embodiment, the superior surface of the block is covered with an adhesive substance to which the end 122' of the band will adhere. One skilled in the art will appreciate that the band may also be fastened by other means comprising: magnets, clips, staples, or clamps.

What is claimed is:

1. A medical tubing stabilization device comprising:
   a block having a superior surface, wherein the superior surface has a central depression that supports medical tubing therein, and wherein the block comprises a compressible material;
   a band including a first end and a second end, wherein the band is capable of extending at least partly around an extremity of a patient such that a gap is provided between the first end of the band and the second end of the band; and
   an attachment device that bridges the gap, wherein the attachment device attaches to the first end of the band and extends from the first end of the band across the superior surface and the medical tubing to be supported in the central depression, and attaches to the band again at the second end of the band such that compression of the block occurs while the medical tubing is secured to the block.

2. The stabilization device of claim 1, wherein the attachment device is tape.

3. The stabilization device of claim 1, wherein the attachment device is a hook and loop fastener.

4. The stabilization device of claim 1, wherein the compressible material allows the central depression to deform around the medical tubing while the medical tubing is secured to the block.

5. The stabilization device of claim 1, wherein the block includes a left side and a right side, wherein the block further includes an inferior surface opposite the superior surface, and wherein the left side and the right side slope toward the inferior surface such that the inferior surface is larger than the superior surface.

6. The stabilization device of claim 1, wherein the medical tubing is a nasotracheal tubing.

7. The stabilization device of claim 1, wherein the extremity is the patient's head.

8. A method of securing medical tubing to a patient, the method comprising the steps in the following order:
   wrapping a band at least partly around an extremity of a patient;
   positioning a block on or in the vicinity of a surface of the extremity, wherein the block has a superior surface, wherein the superior surface has a central depression that supports medical tubing therein, and wherein the block comprises a compressible material;
   securing the block to the band;
   placing the medical tubing in the central depression; and securing the medical tubing to the block via an attachment device extending from the band across the superior surface and the medical tubing placed in the central depression, and attaching to the band again thereby compressing the block while securing the medical tubing to the block.

9. The method of claim 8, wherein the attachment device is tape.

10. The method of claim 8, wherein the attachment device is a hook and loop fastener.

11. The method of claim 8, wherein the compressible material allows the central depression to deform around the medical tubing while securing the medical tubing to the block.

12. The method of claim 8, wherein the block includes a left side and a right side, wherein the block further includes an inferior surface opposite the superior surface, and wherein the left side and the right side slope toward the inferior surface such that the inferior surface is larger than the superior surface.

13. The method of claim 8, wherein the band includes a first end and a second end, and wherein the attachment device is attached to the first end of the band and the second end of the band.

14. The method of claim 8, wherein the medical tubing is a nasotracheal tubing.

15. The method of claim 8, wherein the extremity is the patient's head.

16. A method of securing medical tubing to a patient, the method comprising the steps in the following order:
wrapping a band at least partly around an extremity of a patient such that a gap is provided between a first end of the band and a second end of the band;
positioning a block on or in the vicinity of a surface of the extremity, wherein the block has a superior surface, wherein the superior surface has a central depression that supports medical tubing therein, and wherein the block comprises a compressible material;
securing the block to the band;
placing the medical tubing in the central depression; and
securing the medical tubing to the block via an attachment device that bridges the gap, the attachment device attaching to the first end of the band and extending from the first end of the band across the superior surface and the medical tubing placed in the central depression, and attaching to the band again at the second end of the band thereby compressing the block while securing the medical tubing to the block.

17. The method of claim 16, wherein the attachment device is tape.

18. The method of claim 16, wherein the attachment device is a hook and loop fastener.

19. The method of claim 16, wherein the compressible material allows the central depression to deform around the medical tubing while securing the medical tubing to the block.

20. The method of claim 16, wherein the block includes a left side and a right side, wherein the block further includes an inferior surface opposite the superior surface, and wherein the left side and the right side slope toward the inferior surface such that the inferior surface is larger than the superior surface.

21. The method of claim 16, wherein the medical tubing is a nasotracheal tubing.

22. The method of claim 16, wherein the extremity is the patient's head.

* * * * *